United States Patent

Freiburger et al.

(10) Patent No.: US 6,733,453 B2
(45) Date of Patent: May 11, 2004

(54) ELEVATION COMPOUNDING FOR ULTRASOUND IMAGING

(75) Inventors: Paul D. Freiburger, Seattle, WA (US); Bhaskar S. Ramamurthy, San Jose, CA (US)

(73) Assignee: Siemens Medical Solutions USA, Inc., Iselin, NJ (US)

(*) Notice: Subject to any disclaimer, the term of this patent is extended or adjusted under 35 U.S.C. 154(b) by 0 days.

(21) Appl. No.: 10/234,004

(22) Filed: Sep. 3, 2002

(65) Prior Publication Data

US 2004/0054285 A1 Mar. 18, 2004

(51) Int. Cl.$^7$ ................................................. A61B 8/00
(52) U.S. Cl. ................................................. 600/447
(58) Field of Search ................................. 600/437, 443, 600/447, 459; 73/625–626; 128/916; 310/334–336; 382/128

(56) References Cited

U.S. PATENT DOCUMENTS

| | | | |
|---|---|---|---|
| 5,546,946 A | * | 8/1996 | Souquet ....................... 600/459 |
| 5,653,235 A | | 8/1997 | Teo |
| 5,678,554 A | | 10/1997 | Hossack et al. |
| 5,897,501 A | * | 4/1999 | Wildes et al. ................ 600/447 |
| 5,902,242 A | | 5/1999 | Ustuner et al. |
| 6,043,589 A | | 3/2000 | Hanafy |
| 6,057,632 A | | 5/2000 | Ustuner |
| 6,132,375 A | | 10/2000 | Napolitano |
| 6,464,638 B1 | * | 10/2002 | Adams et al. ................ 600/443 |
| 6,511,426 B1 | * | 1/2003 | Hossack et al. ........... 7600/437 |
| 6,524,247 B2 | * | 2/2003 | Zhao et al. .................. 600/437 |
| 6,527,720 B1 | * | 3/2003 | Ustuner et al. .............. 600/443 |

* cited by examiner

Primary Examiner—Francis J. Jaworski

(57) ABSTRACT

Speckle is reduced by compounding. 1.25, 1.5, 1.75 and 2D arrays are used to obtain frames of data representing a same scan plane, but with different elevation spatial frequency content. The elevation aperture for one frame of data is different than an elevation aperture of another frame of data. The frames of data responsive to the different elevation apertures are compounded, reducing speckle.

26 Claims, 1 Drawing Sheet

ELEVATION COMPOUNDING FOR ULTRASOUND IMAGING

BACKGROUND

The present invention relates to ultrasound imaging with reduced speckle. In particular, ultrasound data associated with different spatial and/or frequency content is compounded. Speckle information in one frame of data is decorrelated with speckle information in another frame of data associated with different spatial or frequency content. By compounding the frames of data, the decorrelated speckle is reduced.

U.S. pat. No. 6,511,426 (U.S. application Ser. No. 09/328, 113) shows reducing speckle through elevation compounding. Frames of data from scan planes having different elevation positions are compounded together. For example, the transducer is translated along the elevation dimension or an elevation aperture is translated in the elevation dimension along a multi-dimensional transducer array. The compounded frames have reduced speckle variation.

U.S. pat. No. 5,653,235 discloses a system for reducing speckle for two-dimensional imaging. A two-dimensional transducer array produces multiple beams at different orientations. A scan plane is rotated to insonify a particular location from different angles. The data for the spatial location is compounded.

Multi-dimensional transducer arrays are also used for imaging without compounding. For example, 1.25D, 1.5D or 1.75D arrays are used to acquire data representing a scan plane. Rows of elements along the elevation dimension are used to electronically or mechanically focus the transmitted energy in the elevation dimension, increasing resolution.

BRIEF SUMMARY

The present invention is defined by the following claims, and nothing in this section should be taken as a limitation on those claims. By way of introduction, the preferred embodiments described below include methods and systems for reducing speckle using compounding with multi-dimensional transducer arrays. 1.25, 1.5, 1.75 and 2D arrays are used to obtain frames of data representing a same scan plane, but with different elevational spatial frequency content. The elevation aperture for one frame of data is different than an elevation aperture of another frame of data. The frames of data responsive to the different elevation apertures are compounded, reducing speckle.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Frames of data associated with different elevational spatial frequency content are compounded together for generating an image with reduced speckle. Using multi-dimensional transducers, such as 1.25, 1.5, 1.75 and 2D arrays, frames of data associated with a same scan plane are acquired using different elevation apertures. Decorrelation of the speckle between the different frames of data reduces the speckle in the compounded image. Using multi-dimensional arrays may allow for frames of data associated with elevation beam patterns having low side lobe levels, narrow beam width and high signal-to-noise ratio for detecting small lesions. Using larger elevation apertures may also allow better identification of curved specular boundaries.

Figure 1:
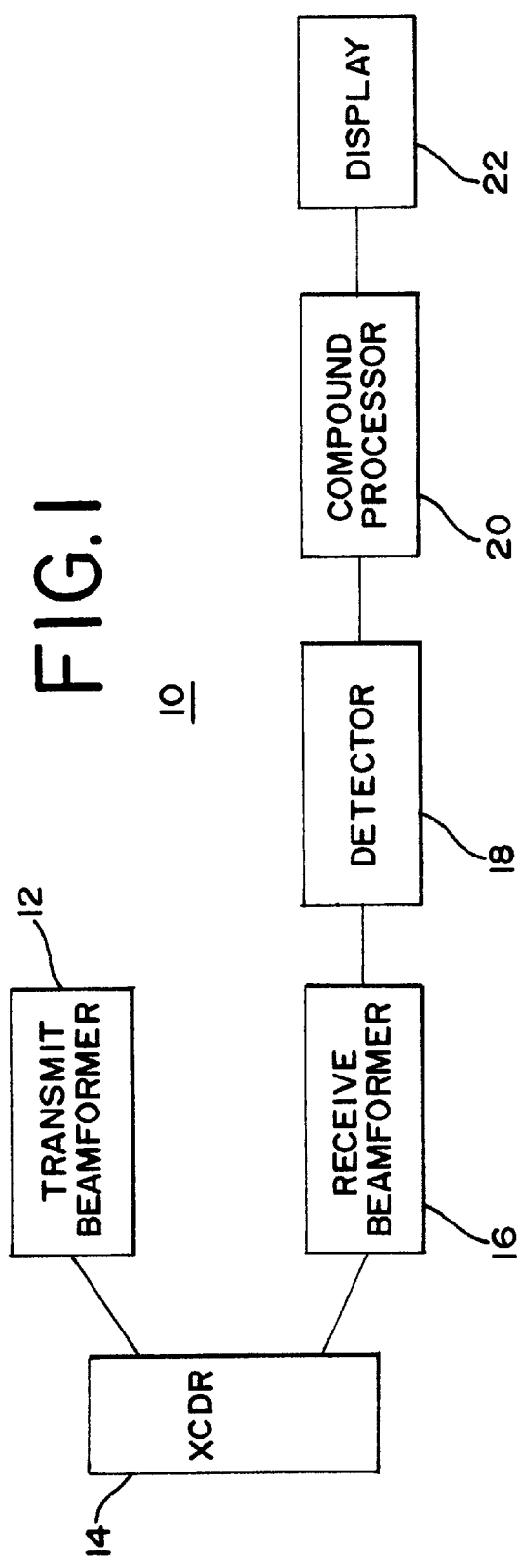
FIG. 1 is a block diagram of one embodiment of an ultrasound system for compounding with different elevation apertures.

FIG. 1 shows an ultrasound system 10 of one embodiment for acquiring ultrasound data with reduced speckle. The system 10 includes a transmit beamformer 12, a transducer 14, a receive beamformer 16, a detector 18, a compound processor 20 and a display 22. Additional, different or fewer components may be provided, such as providing the compound processor 20 and display 22 separately as a computer workstation connected with a source of frames of ultrasound data.

The transmitter 12 comprises a transmit beamformer, such as one or more waveform generators operable to provide delayed and apodized waveforms to the transducer 14. For example, a plurality of memories, amplifiers and other digital and/or analog circuits function in separate channels for focusing the acoustic energy generated by the transducer 14. In alternative embodiments, the transmitter 12 comprises a single channel or a transmitter for generating a plane wave. The transmitter 12 generates electrical signals in successive transmit events. Each transmit event is associated with transmitting acoustic energy into the patient for subsequent receiving of echo signals.

The transmitter 12 includes a plurality of switches for selectively connecting various transmit channels to specific rows or elements of the transducer 14. In alternative embodiments, the switches, such as transistors or microelectromechanical switches are provided in the transducer 14. Additional switches may be provided for switchably connecting either of transmit channels or receive channels to any of the various elements of the transducer 14. The switches allow selection of different apertures, such as different elevation apertures.

The transducer 14 comprises an array of piezoelectric or microelectromechanical elements for transducing between acoustic and electrical energies. The array of elements of the transducer 14 is configured as a multi-dimensional transducer array, such as an N×M array of elements where N and M are greater than 1. The multi-dimensional array has at least two elevation spaced rows of elements. For example, the transducer 14 comprises a 1.25D, 1.5D, 1.75D, or 2D array. A 1.25D array comprises two or more elevationally spaced rows of elements where no relative delay is provided between each of the rows, such as where either a center row or all rows of elements are connected to the same transmit beamformer channels. A 1.5D array comprises three or more elevationally spaced rows of elements where a center and two electrically connected outside or outer rows independently connect to two sets of system channels. All of the rows may be switchably connected to a same set of system channels. A 1.75D array comprises a plurality of elevationally spaced rows that are each independently connectable to sets of system channels, but some switching interconnecting elements of the various elevationally spaced rows may be provided. A two-dimensional array is similar to a 1.75D array, but has a larger number of elevationally spaced rows, such as forming a square array.

The receiver 16 comprises a receive beamformer or other device operable to isolate electrical signals representing acoustical signals from specific spatial locations. In one embodiment, the receiver 16 comprises a plurality of amplifiers, delays and a summer. The amplifiers apply apodization, the delays apply relative delays for focusing and the summer sums the signals from a plurality of elements or channels to form a sample or signal representing a single spatial location. The receiver 16 operates dynamically to change the focus using the apodization and delay profile during a receive event to focus along one or more scan lines.

In one embodiment, the receiver 16 includes separate receive channels or beamformers for connecting to two different apertures at a same time. For example, the receiver 16 connects with two different elevationally spaced apertures, such as connecting with different rows or combinations of rows of elements. The separate apertures may include common elements or rows. The common elements or rows connect with two or more receive channels. In response to a first transmit event, the receiver 16 is operable to receive signals from the two different apertures, and output multiple samples or signals representing the same spatial locations. For a given spatial location, two samples or signals are provided, each associated with a different elevation aperture. In alternative embodiments, the receiver 16 is operable to receive through a single aperture in response to the transmit event. In yet other alternative embodiments, the receiver 16 is operable to receive through three or more separate apertures in response to a single transmit event.

In one embodiment, the receiver 16 includes a filter, such as a baseband filter, a finite impulse response filter, and infinite impulse response filter, a processor implemented filter, an analog implemented filter or other filtering device operable to isolate information at a band of frequencies. In one embodiment, the filter is programmable to select between different possible frequency bands, but a non-programmable filter or a selection of set filters may be provided. The filter is operable to isolate data at different frequency bands, such as isolating information associated with a harmonic (e.g. second harmonic) of a fundamental transmit frequency or information at the fundamental transmit frequency. In one embodiment, two or more separate filters are provided for substantially simultaneously isolating information at two different frequency bands from the same or different apertures. As another example, the filter is operable to isolate information at one fundamental frequency in response to one transmit event and at another or different fundamental frequency in response to a different transmit event.

The transmitter 12 and the receiver 16 are operable to acquire data representing a region of the patient. Any of various scan formats may be used, such as linear, sector, Vector®, curvilinear, other scan formats, and combinations thereof. By maintaining the transducer 14 in one substantially same position, data associated with two different elevation apertures representing a same spatial location or spatial locations within a same scan plane are acquired. Substantially is used with position to account for motion of the patient, breathing by the patient, or unintentional motion by an operator holding the transducer 14. Using electrical or mechanical focus along the elevation dimension, the transducer 14 is operable to transmit and receive along scan lines in a same scan plane from the different apertures. For example, one elevation aperture comprises a left or bottom aperture of a bottom row and a center row of elevationally spaced elements and a second aperture comprises a right or top aperture of a top row and the center row of elevationally spaced elements. The left (i.e. bottom) aperture and right (i.e. top) aperture overlap, both using the center row of elements. Using either a mechanical or electrical focus, both the left and right (i.e. bottom and top) overlapping apertures transmit and receive within the same scan plane. For example, the transmit focus point and the dynamic receive focal points are within the same scan plane. In alternative embodiments, the elevationally spaced rows are close enough together relative to the beam width that no or minimal mechanical or electrical focus provides for scanning within a same scan plane.

Figure 2:
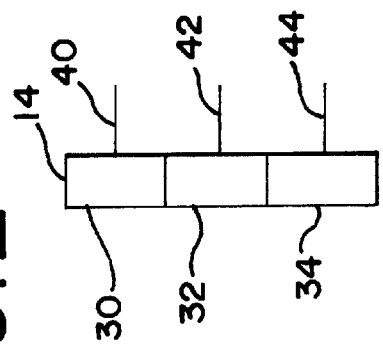
FIG. 2 is a graphical representation of one embodiment of a cross section of a multi-dimensional transducer array.

FIG. 2 shows one embodiment of a cross-section of the multi-dimensional transducer 14 with three elevationally spaced rows 30, 32, and 34 of elements. Three elevationally spaced rows are provided, but two, four or more elevationally spaced rows may be used. Any number of elements may be positioned within a row on the azimuthal dimension. A signal line 40, 42 and 44 connects with each of the elements such as the elevationally spaced elements 30, 32 and 34, respectively. The elevation aperture is responsive to the interconnection of the signal lines 40, 42 and 44 with system channels. For example, where the transducer 14 is a 1.25D array, the center row 32 comprises one elevation aperture by connecting the signal line 42 to a system channel. A second elevational spaced aperture is provided by connecting all of the rows 30, 32 and 34 and the associated signal lines 40, 42, and 44 together to a same system channel. As another example, a 1.5D array provides for the center row 32 and associated signal lines 42 as one aperture. A second elevational aperture comprises the outer rows 30 and 34 and associated signal lines 40 and 44 switched together to a same system channel. All three rows 30, 32, 34 may be switched together in an alternative embodiment. As yet another example for a 1.75D or 2D array, each of the rows 30, 32 and 34 and associated signal lines 40, 42 and 44 are independently connectable to different system channels, but may be switched together. Any one or combination of two or more of the rows 30, 32 and 34 define an elevation aperture. Each of multiple rows in a given elevation aperture may either be switched together to connect the same system channel or connect independently to separate system channels.

The detector 18 comprises a B-mode detector, Doppler detector, flow detector or other circuit for detecting signal characteristics, such as intensity, tissue or fluid energy, tissue or fluid velocity, or tissue or fluid variance. Frames of data responsive to different elevation apertures but representing spatial locations in a same scan plane are input to the detector 18. The detector 18 outputs frames of detected data representing the same scan plane but responsive to different elevation apertures. Where the receiver 16 is operable to output two frames of data representing the scan plane but responsive to different elevation apertures at substantially a same time, the detector 18 includes a buffer for sequentially detecting from the frames of data or includes parallel processing paths for substantially simultaneously detecting from the different frames of data.

The compound processor 20 comprises a general processor, a digital signal processor, an application specific integrated circuit, a summer and multipliers, a summer, a filter, an analog device, a digital device, a memory or combinations thereof. The compound processor 20 receives two or more frames of detected data representing a same scan plane. Where the two frames of data are provided sequentially, a buffer or other memory device stores at least one of the frames of data so that the frames are available for compounding. The compound processor 20 compounds detected data, but data prior to detection may alternatively be compounded. The detected data is either scan converted or in a scan format. The compound processor 20 implements an averaging of data representing same spatial locations within the scan plane. Weighted averaging, lookup table combination, linear, nonlinear or other functions for combining two or more data representing a same spatial location into a single output value may be used.

The display 22 comprises a CRT, monitor, LCD, flat screen or other device for displaying an image responsive to two different elevation apertures. The display 22 may also include a scan converter for converting from a scan format to a display or Cartesian coordinate format. The image has reduced speckle as compared to an image generated without compounding of frames of data responsive to different elevation apertures.

Figure 3:
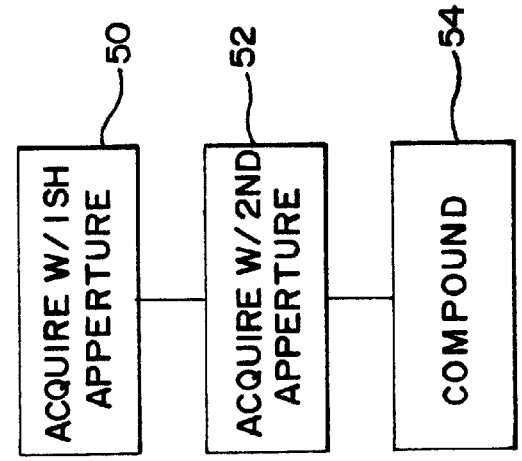
FIG. 3 is a flowchart diagram of one embodiment of a method for reducing speckle.

FIG. 3 is a flow chart representing one embodiment of a method for acquiring ultrasound data with reduced speckle. Multiple frames of data of a target are obtained in response to different elevation apertures of a non-moving multi-dimensional transducer array. For example, data associated with first and second elevation apertures are acquired in acts 50 and 52. The data is then compounded in act 54. Different frames of data are combined to form an elevationally compounded image. A frame of data includes one or more of image data, scan converted data, detected data, incoherent data or other collection of data representing an area at a given time or range of times.

Each frame of data associated with a different elevation aperture of the multi-dimensional transducer array represents the same scan plane. Using electronic or mechanical focus, the elevation width of each beam responsive to each of the different elevation apertures sufficiently ride to insonify the same scan plane or same spatial location. Full decorrelation between component beams or two-way response associated with the different elevation apertures is provided where the spectrum of the component beams is separated by about 6 dB of bandwidth. More separation may not further reduce speckle variance but may reduce the bandwidth of the component beams given that the total bandwidth is limited by the physical size of the aperture.

In one embodiment, the elevation beam pattern of the two-way response has low side lobes and a narrow beam width for a high signal-to-noise ratio. Wider elevation apertures provide increased contrast resolution and better signal-to-noise ratios. A large transmit elevation aperture is desired for harmonic imaging. A continuous elevation aperture provides for a well-defined or predictable beam pattern and avoids or minimizes tissue aberration artifacts.

The frames of data are acquired sequentially, such as transmitting and receiving with a first elevation aperture subsequent to transmitting and receiving with a second aperture. In other embodiments, acoustic energy is transmitted from the multi-dimensional transducer 14 in a first event and the frames of data associated with the different elevation apertures are acquired substantially simultaneously or in response to the same transmit event. The frames of data are then separately receive beamformed to generate the two different frames of data. Since the receive apertures are two different elevation apertures, the overall two-way response or equivalent apertures are different even with the same transmit aperture.

For either of sequential or simultaneous acquisition, the transmit aperture used may be the same as one of either of the two different receive elevation apertures or may be yet a third or different elevation aperture. Better signal-to-noise ratio is provided by transmitting from the entire elevation aperture. The whole elevation aperture may be used with a tapered elevation apodization for better near field performance and lower side lobes, but may be equally apodized across the elevation aperture. For better near field performance, the center row of elements or a grouping of center rows of elements are used for the transmit aperture.

In one embodiment, the different receive apertures include at least one row of elements common to the different elevation apertures. For example, a center row of elements are common to asymmetric or left and right (i.e. bottom and top) overlapping receive apertures. Wide overlapping apertures with left-right (i.e. bottom-top) asymmetry may be used with one, two or more rows of elements in common and one, two or more rows of elements unique to each of the left or right (i.e. bottom or top) apertures. Different receive apertures with no overlap may be used.

For receiving data from two different elevation apertures in response to one transmit event, elevation transmit focal depth aperture overlap may provide an optimal aperture overlap at the transmit focal depth. Around the transmit focus, there is a region of optimal focusing. Receive can be focused at all depths, but each transmit is focused to one or a limited number of depths. The image is optimally focused around the transmit focus. Multiple transmit foci or a line focus extends the region of optimal focus. Deep depth resolution and signal-to-noise ratio may be enhanced with elevation apertures that are a function of the azimuthal focal depth using the sequential transmit and receive acquisition. The elevation extent of the receive apertures or the rows of elements used may change as a function of the selected azimuthal focal depth.

In one embodiment, both of the receive, transmit or receive and transmit elevation apertures are continuous, such as including all rows of elements between the edges of the elevation aperture. For example, an elevation aperture of any one of the rows 30, 32 and 34 of FIG. 2 is a continuous aperture. Left or right (i.e. bottom or top) apertures of rows 30 and 32 or 32 and 34, respectively, are continuous. The entire aperture including rows 30, 32 and 34 is continuous, but rows 30 and 34 connected in an aperture without the center row 32 are not continuous.

The different elevation apertures used as either receive apertures or both transmit and receive apertures vary as a function of the type of transducer 14. For a 1.25D array, a single row of elements is used for one elevation aperture. A second elevationally spaced row is switched with the single row and used as the second elevation aperture. The frame of data associated with the two or more switched together rows has a different spatial frequency content as a result of the 50 percent overlap in the elevation aperture.

For a 1.5D array, one elevation aperture is a center row or rows. The different elevation aperture is the outer rows on each side of the center row or the outer rows and the center row. Different spatial frequency content results from the non-overlapping or partially overlapping elevation apertures. Any of various combinations of transmit and receive apertures may be used, such as transmitting from three rows and receiving on the center row and then transmitting from two outer rows and receiving on the two outer rows.

For a 1.75D or 2D array, any of various combinations of rows or selected single rows are used to form the two different elevation apertures. At least one row of elements is used in one elevation aperture and not in another elevation aperture. For example, one row, such as a bottom row, is used for transmitting and receiving acoustic information. Subsequently, a center row is used to acquire information for another frame of data. A top or another edge row is then used to acquire a third frame of data. Since three different elevation apertures are used, each frame of data is associated with a different spatial frequency content. In alternative embodiments, overlapping apertures, only two apertures, or four or more different elevation apertures may be used. A two-dimensional array may operate similar to a 1.75D array, but with additional elevation spaced rows of elements for use in any given elevation aperture. Any of various combinations of transmit and receive apertures may be used, such as transmitting with all three rows for each of the receptions in the 1.75D example above.

In one embodiment, speckle is reduced using frequency compounding in addition to using different elevation apertures. A first frame of data is acquired in response to one frequency band and the second frame of data is acquired in response to a different frequency band. For example, both frames of data are associated with the same transmit frequency but received at the fundamental frequency and a harmonic of the fundamental frequency. For example, a frame of data acquired using a center row of elements as the elevation aperture is acquired at a fundamental or transmitted frequency band. A second frame of data associated with an elevation aperture of three rows is received at a second harmonic of the fundamental transmit frequency. The harmonic frequencies may be used for imaging added contrast agents or for imaging tissue free of added contrast agents for an entire imaging session. As another example, the first frame of data is associated with a harmonic of a first fundamental transmit frequency, and a second frame of data is associated with a same or different harmonic of a different or same fundamental transmit frequency. In alternative embodiments, the frames of data are acquired in response to the same transmit and receive frequencies and the same bandwidths.

In act 54, the first and second frames of data are compounded for each of a plurality of spatial locations. A datum from one frame of data is compounded with a datum from the other frame of data for each spatial location. The compounding comprises a summation, multiplication, linear, nonlinear or other combination function. For example, the data is averaged. A weighted averaging may be used, such as weighting a frame of data associated with higher resolution, such as harmonic frequency data, more greatly than other frames of data. Two, three or a greater number of frames of data may be compounded.

The data compounded comprises detected pre-scan converted data. Where a same scan format is used for each frame of data, the same spatial locations are represented in each frame of data. Where different scan formats are used, the compounding may involve interpolation, extrapolation, spatial averaging or selection of data representing a location closest to the desired spatial location. In yet other alternative embodiments, correlation techniques are used for spatially aligning one frame of data relative to another frame of data to counteract unintentional movement of the transducer 14 or the patient. In yet other alternative embodiments, scan converted data is compounded. In other embodiments, data is compounded prior to detection with or without accounting for relative phase shifts or the coherence of the data.

In one embodiment, a running average of frames of data associated with different elevation apertures outputs compound images or frames of data at a same rate as the frame acquisition rate. For example, the different elevation apertures are repeated. For any two or three sequentially acquired frames of data, each frame is associated with a different elevation aperture. A moving window is then applied to the frames of data for compounding. By using parallel receive beamformation techniques, such as receiving using two different elevation apertures in response to a same transmit event, compounding is provided without reducing the acquisition rate and associated output frame rate or display rate. In alternative embodiments, the compounded image frames are output at a slower rate than the acquisition rate, such as associated with inputting two frames of data associated with different elevation apertures and outputting a single compound frame. The two input frames are then discarded, and the next compounded image frame is responsive to two different frames of data.

In one embodiment, a transducer with a frequency dependent elevation aperture is used to scan a same plane with different bandwidths. For example, the transducers disclosed in Hanafy, U.S. pat. No. 6,043,589 "Two Dimensional Transducer Array and the Method of Manufacture thereof", in Hossack et al., U.S. pat. 5,678,554 "Ultrasound Transducer for Multiple Focusing and Method for Manufacture Thereof" and in Ustuner U.S. pat. No. 6,057,632 "Frequency and Bandwidth Controlled Ultrasound Transducer", the disclosures of which are incorporated herein by reference are used with different frequency bands acquire different data representing a scan plane. In another embodiment, the frequency responsive dual elevation element transducer disclosed provisional application No. 60/386,324, the disclosure of which is incorporated herein by reference, is used with different frequencies or bandwidths to acquire different data representing a same scan plane.

While the invention has been described above by reference to various embodiments, it should be understood that many changes and modifications can be made without departing from the scope of the invention. For example, scan lines with different orientations but beam width sufficient to cover the scan plane or spatial locations of interest within a range of depths adjacent to or spaced from the transducer may be used to scan a same scan plane. Any of various combinations of different or same transmit and receive apertures may be provided. The different elevation apertures may be used in combination with the same or different azimuth apertures for any one or all of the rows. Other elevation or azimuth aperture compounding techniques or other techniques for reducing speckle may be used in combination with the elevation aperture compounding disclosed herein.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for acquiring ultrasound data with reduced speckle, the method comprising:

(a) acquiring first data representing a first scan plane with a first elevation aperture of a multi-dimensional transducer array of elements;

(b) acquiring second data representing the first scan plane with a second elevation aperture of the multi-dimensional transducer array of elements, the second elevation aperture having at least one different element than the first elevation aperture; and (c) compounding the first and second data.

2. The method of claim 1 wherein repeating (a), (b) and (c) such that an acquisition rate is about a display rate.

3. The method of claim 1 wherein (a) comprises acquiring the first data with a first row of elements of a 1.25D transducer array, and (b) comprises acquiring the second data with the first row and a second row of elements of the 1.25D transducer array switched together.

4. The method of claim 1 wherein (a) comprises acquiring the first data with a center row of elements of a 1.5D transducer array, and (b) comprises acquiring the second data with at least two outer rows of elements of the 1.5D transducer array.

5. The method of claim 1 wherein (a) comprises acquiring the first data with a first row of elements of a 1.75D transducer array and (b) comprises acquiring the second data with a second row of elements of the 1.75D transducer array, the second row different than the first row.

6. The method of claim 5 further comprising:
(d) acquiring third data representing the first spatial location with a third elevation aperture of the 1.75D transducer array, the third elevation aperture different than the first and second elevation apertures;
wherein (c) comprises compounding the first, second and third data.

7. The method of claim 1 wherein (a) comprises acquiring the first data with a first row of elements of a 2D transducer array and (b) comprises acquiring the second data with a second row of elements of the 2D transducer array, the second row different than the first row.

8. The method of claim 1 wherein (a) and (b) comprise transmitting from the multi-dimensional transducer array in a first event, (a) comprises receiving with the first aperture in response to the first event and (b) comprises receiving with the second aperture in response to the first event;
further comprising:
(d) separately receive beamforming the first and second data.

9. The method of claim 1 wherein (a) comprises transmitting and receiving with the first aperture and (b) comprises, subsequent to (a), transmitting and receiving with the second aperture.

10. The method of claim 1 wherein the first aperture includes at least one row of elements also included in the second aperture.

11. The method of claim 10 wherein the first aperture comprises a bottom aperture and the second aperture comprises a top aperture, the bottom aperture overlapping with the top aperture.

12. The method of claim 1 wherein both the first and second aperture comprise continuous apertures.

13. The method of claim 1 wherein (a) comprises acquiring the first data in response to a first frequency and (b) comprises acquiring the second data in response to a second frequency, the second frequency different than the first frequency.

14. The method of claim 13 wherein the second frequency is a harmonic of a fundamental transmit frequency and (b) comprises acquiring the second data from tissue free of added contrast agent during an entire imaging session.

15. The method of claim 1 wherein (a) and (b) comprise acquiring the first and second data in response to same transmit and receive frequencies and bandwidths.

16. The method of claim 1 wherein the first and second data comprise detected data and (c) comprises compounding detected data.

17. The method of claim 1 wherein the first elevation aperture is entirely free of overlapping elements with the second elevation aperture.

18. An ultrasound system for acquiring ultrasound data with reduced speckle, the system comprising:
a multi-dimensional transducer array having at least two elevation spaced rows of elements;
a transmitter connected with the multi-dimensional transducer array;
a receiver connected with the multi-dimensional transducer array;
wherein the transmitter and receiver are operable to acquiring first and second data both representing a first scan plane with first and second elevation apertures, respectively, of the multi-dimensional transducer array, the second elevation aperture having at least one different element than the first elevation aperture; and
a compound processor operable to compound the first and second data.

19. The system of claim 18 wherein the multi-dimensional transducer array comprises a 1.25D array of at least two rows of elements, the first aperture comprising a first row of elements and the second aperture comprising the first and another row of elements switched together to the transmitter and the receiver.

20. The system of claim 18 wherein the multi-dimensional transducer array comprises a 1.5D array with at least three rows of elements, the first aperture comprising a center row of elements and the second aperture comprising at least two outer rows of elements switched together to the transmitter and the receiver.

21. The system of claim 18 wherein the multi-dimensional transducer array comprises one of a 1.75D and 2D array with at least three rows of elements, the first aperture comprising a first row of elements and the second aperture comprising a second row of elements, the second row different than the first row.

22. The system of claim 18 wherein the transmitter comprises a transmit beamformer and the receiver comprises a receive beamformer, the transmit beamformer operable to transmit from the multi-dimensional transducer array in a first event, and the receive beamformer having separate channels connected to the first and second apertures, the receive beamformer operable to receive with the first aperture in response to the first event and receive with the second aperture in response to the first event.

23. The system of claim 18 wherein the first aperture comprises a bottom aperture and the second aperture comprises a top aperture, the bottom aperture overlapping with the top aperture.

24. The system of claim 18 wherein the receiver further comprises a filter operable to acquire the first data in response to a first frequency and acquire the second data in response to a second frequency, the second frequency different than the first frequency.

25. The system of claim 24 wherein the second frequency is operable to acquire data in response to a harmonic of the first frequency.

26. The system of claim 18 further comprising:
a detector operable to detect the first and second data;
wherein compound processor is operable to compound the first and second detected data.

* * * * *